United States Patent
Layman (10) Patent No.: US 7,905,942 B1
(45) Date of Patent: Mar. 15, 2011

(54) MICROWAVE PURIFICATION PROCESS

(75) Inventor: Fredrick P. Layman, Carefree, AZ (US)

(73) Assignee: SDCmaterials, Inc., Tempe, AZ (US)

( * ) Notice: Subject to any disclaimer, the term of this patent is extended or adjusted under 35 U.S.C. 154(b) by 499 days.

(21) Appl. No.: 12/152,095

(22) Filed: May 9, 2008

Related U.S. Application Data (60) Provisional application No. 60/928,946, filed on May 11, 2007.

(51) Int. Cl.
*C22B 9/14* (2006.01)
*C22B 9/22* (2006.01)

(52) U.S. Cl. ............ 75/345; 75/10.13; 75/585; 423/298

(58) Field of Classification Search ............ 75/345, 75/10.13, 585; 423/298
See application file for complete search history.

(56) References Cited

U.S. PATENT DOCUMENTS

| | | | |
|---|---|---|---|
| 2,419,042 A | 4/1947 | Todd | 202/205 |
| 2,519,531 A | 8/1950 | Worn | 230/95 |
| 2,562,753 A | 7/1951 | Trost | |
| 2,689,780 A | 9/1954 | Rice | 23/106 |
| 3,001,402 A | 9/1961 | Koblin | 73/421.5 |
| 3,067,025 A | 12/1962 | Chisholm | |
| 3,178,121 A | 4/1965 | Wallace, Jr. | |
| 3,401,465 A | 9/1968 | Larwill | |
| 3,457,788 A | 7/1969 | Miyajima | 73/422 |
| 3,537,513 A | 11/1970 | Austin et al. | 165/70 |
| 3,741,001 A | 6/1973 | Fletcher et al. | 73/28 |
| 3,774,442 A | 11/1973 | Gustavsson | 73/28 |
| 3,959,420 A | 5/1976 | Geddes et al. | 261/112 |
| 4,008,620 A | 2/1977 | Narato et al. | 73/421.5 A |
| 4,018,388 A | 4/1977 | Andrews | |
| 4,139,497 A | 2/1979 | Castor et al. | |
| 4,171,288 A | 10/1979 | Keith et al. | |
| 4,248,387 A | 2/1981 | Andrews | |
| 4,284,609 A | 8/1981 | deVries | |
| 4,388,274 A | 6/1983 | Rourke et al. | |
| 4,436,075 A | 3/1984 | Campbell et al. | 123/557 |
| 4,513,149 A | 4/1985 | Gray et al. | |
| 4,764,283 A | 8/1988 | Ashbrook et al. | |

(Continued)

FOREIGN PATENT DOCUMENTS

JP 56-146804 11/1981

(Continued)

OTHER PUBLICATIONS

Kenvin et al. "Supported Catalysts Prepared from Monoclear Copper Complexes: Catalytic Properties", Journal of Catalysis, pp. 81-91, 1992.

(Continued)

*Primary Examiner* — George Wyszomierski
*Assistant Examiner* — Tima M McGuthry-Banks
(74) *Attorney, Agent, or Firm* — Haverstock & Owens LLP (57) ABSTRACT

A method of purifying a target powder having an oxygen content, the method comprising: flowing hydrogen gas through a microwave production chamber; applying microwaves to the hydrogen gas as the hydrogen gas flows through the microwave production chamber, thereby forming hydrogen radicals from the hydrogen gas; flowing the hydrogen radicals out of the microwave production chamber to the target powder disposed outside of the microwave production chamber; and applying the hydrogen radicals to the target powder, thereby removing a portion of the oxygen content from the powder. Preferably, the target powder is agitated as the hydrogen radicals are being applied.

11 Claims, 7 Drawing Sheets

U.S. PATENT DOCUMENTS

| | | | | |
|---|---|---|---|---|
| 4,824,624 | A | 4/1989 | Palicka et al. | 264/67 |
| 4,855,505 | A | 8/1989 | Koll | |
| 4,983,555 | A | 1/1991 | Roy et al. | 501/120 |
| 4,987,033 | A | 1/1991 | Abkowitz et al. | 428/469 |
| 5,043,548 | A | 8/1991 | Whitney et al. | 219/121.84 |
| 5,073,193 | A | 12/1991 | Chaklader et al. | 75/346 |
| 5,369,241 | A | 11/1994 | Taylor et al. | 219/121.47 |
| 5,371,049 | A | 12/1994 | Moffett et al. | 501/89 |
| 5,372,629 | A | 12/1994 | Anderson et al. | 75/332 |
| 5,392,797 | A | 2/1995 | Welch | 134/108 |
| 5,439,865 | A | 8/1995 | Abe et al. | |
| 5,485,941 | A | 1/1996 | Guyomard et al. | 222/1 |
| 5,534,149 | A | 7/1996 | Birkenbeil et al. | |
| 5,553,507 | A | 9/1996 | Basch et al. | 73/863.01 |
| 5,611,896 | A | 3/1997 | Swanepoel et al. | 204/169 |
| 5,630,322 | A | 5/1997 | Heilmann et al. | 62/95 |
| 5,749,938 | A | 5/1998 | Coombs | 75/332 |
| 5,776,359 | A | 7/1998 | Schultz et al. | 252/62.51 |
| 5,788,738 | A | 8/1998 | Pirzada et al. | 75/331 |
| 5,811,187 | A | 9/1998 | Anderson et al. | 428/403 |
| 5,851,507 | A | 12/1998 | Pirzada et al. | |
| 5,853,815 | A | 12/1998 | Muehlberger | 427/446 |
| 5,905,000 | A | 5/1999 | Yadav et al. | 429/33 |
| 5,935,293 | A | 8/1999 | Detering et al. | 75/10.29 |
| 5,989,648 | A | 11/1999 | Phillips | 427/456 |
| 5,993,967 | A | 11/1999 | Brotzman, Jr. et al. | 428/407 |
| 5,993,988 | A | 11/1999 | Ohara et al. | 429/40 |
| 6,012,647 | A | 1/2000 | Ruta et al. | 239/132.1 |
| 6,033,781 | A | 3/2000 | Brotzman, Jr. et al. | 428/405 |
| 6,059,853 | A | 5/2000 | Coombs | 75/332 |
| 6,102,106 | A | 8/2000 | Manning et al. | 165/76 |
| 6,214,195 | B1 | 4/2001 | Yadav et al. | 205/334 |
| 6,228,904 | B1 | 5/2001 | Yadav et al. | 523/210 |
| 6,254,940 | B1 | 7/2001 | Pratsinis et al. | 427/562 |
| 6,261,484 | B1 | 7/2001 | Phillips et al. | 264/5 |
| 6,267,864 | B1 | 7/2001 | Yadav et al. | 205/341 |
| 6,344,271 | B1 | 2/2002 | Yadav et al. | 428/402 |
| 6,379,419 | B1 | 4/2002 | Celik et al. | 75/346 |
| 6,387,560 | B1 | 5/2002 | Yadav et al. | 429/45 |
| 6,395,214 | B1 | 5/2002 | Kear et al. | 264/434 |
| 6,398,843 | B1 | 6/2002 | Tarrant | 75/249 |
| 6,409,851 | B1 | 6/2002 | Sethuram et al. | 148/565 |
| 6,413,781 | B1 | 7/2002 | Geis et al. | |
| 6,416,818 | B1 | 7/2002 | Aikens et al. | 427/383.1 |
| RE37,853 | E | 9/2002 | Detering et al. | 75/10.19 |
| 6,444,009 | B1 | 9/2002 | Liu et al. | 75/332 |
| 6,517,800 | B1 | 2/2003 | Cheng et al. | 423/447.1 |
| 6,524,662 | B2 | 2/2003 | Jang et al. | 427/535 |
| 6,531,704 | B2 | 3/2003 | Yadav et al. | 250/493.1 |
| 6,554,609 | B2 | 4/2003 | Yadav et al. | 432/9 |
| 6,562,495 | B2 | 5/2003 | Yadav et al. | 429/12 |
| 6,569,397 | B1 * | 5/2003 | Yadav et al. | 423/345 |
| 6,569,518 | B2 | 5/2003 | Yadav et al. | 428/323 |
| 6,572,672 | B2 | 6/2003 | Yadav et al. | 75/343 |
| 6,596,187 | B2 | 7/2003 | Coll et al. | |
| 6,603,038 | B1 | 8/2003 | Hagemeyer et al. | |
| 6,607,821 | B2 | 8/2003 | Yadav et al. | 428/323 |
| 6,610,355 | B2 | 8/2003 | Yadav et al. | 427/115 |
| 6,635,357 | B2 | 10/2003 | Moxson et al. | 428/548 |
| 6,641,775 | B2 | 11/2003 | Vigliotti et al. | 264/618 |
| 6,652,822 | B2 | 11/2003 | Phillips et al. | 423/290 |
| 6,652,967 | B2 | 11/2003 | Yadav et al. | 428/403 |
| 6,669,823 | B1 | 12/2003 | Sarkas et al. | 204/164 |
| 6,682,002 | B2 | 1/2004 | Kyotani | 239/318 |
| 6,689,192 | B1 | 2/2004 | Phillips et al. | 75/342 |
| 6,699,398 | B1 | 3/2004 | Kim | 216/55 |
| 6,706,097 | B2 | 3/2004 | Zornes | 96/153 |
| 6,713,176 | B2 | 3/2004 | Yadav et al. | 428/402 |
| 6,716,525 | B1 | 4/2004 | Yadav et al. | 428/402 |
| 6,746,791 | B2 | 6/2004 | Yadav et al. | 429/30 |
| 6,772,584 | B2 | 8/2004 | Chun et al. | 60/275 |
| 6,786,950 | B2 | 9/2004 | Yadav et al. | 75/346 |
| 6,813,931 | B2 | 11/2004 | Yadav et al. | 73/31.05 |
| 6,817,388 | B2 | 11/2004 | Tsangaris et al. | 141/82 |
| 6,832,735 | B2 | 12/2004 | Yadav et al. | 241/16 |
| 6,838,072 | B1 | 1/2005 | Kong et al. | 423/594.2 |
| 6,855,426 | B2 | 2/2005 | Yadav | 428/403 |
| 6,855,749 | B1 | 2/2005 | Yadav et al. | 523/105 |
| 6,886,545 | B1 | 5/2005 | Holm | 123/568.21 |
| 6,896,958 | B1 | 5/2005 | Cayton et al. | 428/323 |
| 6,902,699 | B2 | 6/2005 | Fritzemeier et al. | 419/38 |
| 6,916,872 | B2 | 7/2005 | Yadav et al. | 524/430 |
| 6,919,527 | B2 | 7/2005 | Boulos et al. | 219/121.52 |
| 6,933,331 | B2 | 8/2005 | Yadav et al. | 523/210 |
| 6,986,877 | B2 | 1/2006 | Takikawa et al. | 423/447.3 |
| 6,994,837 | B2 | 2/2006 | Boulos et al. | 423/613 |
| 7,007,872 | B2 | 3/2006 | Yadav et al. | 241/1 |
| 7,052,777 | B2 | 5/2006 | Brotzman, Jr. et al. | 428/570 |
| 7,073,559 | B2 | 7/2006 | O'Larey et al. | 164/76.1 |
| 7,081,267 | B2 | 7/2006 | Yadav | 427/115 |
| 7,101,819 | B2 | 9/2006 | Rosenflanz et al. | 501/10 |
| 7,147,544 | B2 | 12/2006 | Rosenflanz | 451/28 |
| 7,147,894 | B2 | 12/2006 | Zhou et al. | 427/256 |
| 7,166,198 | B2 | 1/2007 | Van Der Walt et al. | 204/165 |
| 7,166,663 | B2 | 1/2007 | Cayton et al. | 524/430 |
| 7,172,649 | B2 | 2/2007 | Conrad et al. | 106/35 |
| 7,178,747 | B2 | 2/2007 | Yadav et al. | 241/23 |
| 7,208,126 | B2 | 4/2007 | Musick et al. | 423/69 |
| 7,211,236 | B2 | 5/2007 | Stark et al. | 423/592.1 |
| 7,217,407 | B2 | 5/2007 | Zhang | 423/610 |
| 7,220,398 | B2 | 5/2007 | Sutorik et al. | |
| 7,307,195 | B2 | 12/2007 | Polverejan et al. | 585/443 |
| 7,323,655 | B2 | 1/2008 | Kim | 219/121.43 |
| 7,384,447 | B2 | 6/2008 | Kodas et al. | 75/332 |
| 7,494,527 | B2 | 2/2009 | Jurewicz et al. | |
| 7,572,315 | B2 | 8/2009 | Boulos et al. | |
| 7,611,686 | B2 * | 11/2009 | Alekseeva et al. | 423/276 |
| 7,615,097 | B2 | 11/2009 | McKechnie et al. | |
| 7,622,693 | B2 | 11/2009 | Foret | |
| 2001/0042802 | A1 | 11/2001 | Youds | |
| 2002/0068026 | A1 | 6/2002 | Murrell et al. | |
| 2002/0079620 | A1 | 6/2002 | Dubuis et al. | 264/328.14 |
| 2003/0036786 | A1 | 2/2003 | Duren et al. | 607/96 |
| 2003/0066800 | A1 | 4/2003 | Saim et al. | |
| 2003/0108459 | A1 | 6/2003 | Wu et al. | 422/186.04 |
| 2003/0172772 | A1 * | 9/2003 | Sethuram et al. | 75/10.19 |
| 2003/0223546 | A1 | 12/2003 | McGregor et al. | 378/143 |
| 2004/0009118 | A1 | 1/2004 | Phillips et al. | |
| 2004/0023453 | A1 | 2/2004 | Xu et al. | |
| 2004/0103751 | A1 | 6/2004 | Joseph et al. | 75/10.19 |
| 2004/0167009 | A1 | 8/2004 | Kuntz et al. | 501/95.2 |
| 2004/0251017 | A1 | 12/2004 | Pillion et al. | 165/289 |
| 2005/0000321 | A1 | 1/2005 | O'Larey et al. | 75/952 |
| 2005/0000950 | A1 | 1/2005 | Schroder et al. | 219/121.59 |
| 2005/0077034 | A1 | 4/2005 | King | 165/163 |
| 2005/0097988 | A1 | 5/2005 | Kodas et al. | 75/332 |
| 2005/0220695 | A1 | 10/2005 | Abatzoglou et al. | |
| 2005/0233380 | A1 | 10/2005 | Pesiri et al. | 435/7.1 |
| 2005/0240069 | A1 | 10/2005 | Polverejan et al. | 585/444 |
| 2005/0258766 | A1 | 11/2005 | Kim | 315/111.21 |
| 2006/0051505 | A1 | 3/2006 | Kortshagen et al. | 427/212 |
| 2006/0068989 | A1 | 3/2006 | Ninomiya et al. | |
| 2006/0096393 | A1 | 5/2006 | Pesiri | 73/863.21 |
| 2006/0105910 | A1 | 5/2006 | Zhou et al. | |
| 2006/0108332 | A1 | 5/2006 | Belashchenko | 219/121.47 |
| 2006/0153728 | A1 | 7/2006 | Schoenung et al. | |
| 2006/0153765 | A1 | 7/2006 | Pham-Huu et al. | |
| 2006/0159596 | A1 | 7/2006 | De La Veaux et al. | 422/151 |
| 2006/0231525 | A1 | 10/2006 | Asakawa et al. | 216/56 |
| 2007/0063364 | A1 | 3/2007 | Hsiao et al. | 264/5 |
| 2007/0084308 | A1 | 4/2007 | Nakamura et al. | 75/346 |
| 2007/0084834 | A1 | 4/2007 | Hanus et al. | 219/121.5 |
| 2007/0087934 | A1 | 4/2007 | Martens et al. | 502/214 |
| 2007/0173403 | A1 | 7/2007 | Koike et al. | |
| 2007/0253874 | A1 | 11/2007 | Foret | |
| 2008/0105083 | A1 | 5/2008 | Nakamura et al. | |
| 2008/0277267 | A1 | 11/2008 | Biberger et al. | |

FOREIGN PATENT DOCUMENTS

| | | |
|---|---|---|
| WO | WO 02/092503 A1 | 11/2002 |
| WO | 2004052778 A2 | 6/2004 |
| WO | WO 2006/079213 A1 | 8/2006 |

OTHER PUBLICATIONS

National Aeronautics and Space Administration, "Enthalpy", http://www.grc.nasa.gov/WWW/K-12/airplane/enthalpy.html, Nov. 23, 2009, 1 page.

Han et al., Deformation Mechanisms and Ductility of Nanostructured Al Alloys, Mat. Res. Soc. Symp. Proc. vol. 821, Jan. 2004, Material Research Society, http://www.mrs.org/s_mrs/bin.asp?CID=2670&DOC=FILE.PDF., 6 pages.

J. Heberlein, "New Approaches in Thermal Plasma Technology", Pure Appl. Chem., vol. 74, No. 3, 2002, pp. 327-335.

T. Yoshida, "The Future of Thermal Plasma Processing for Coating", Pure & Appl. Chem., vol. 66, No. 6, 1994 pp. 1223-1230.

A. Gutsch et al., "Gas-Phase Production of Nanoparticles", Kona No. 20, 2002, pp. 24-37.

Dr. Heike Mühlenweg et al., "Gas-Phase Reactions—Open Up New Roads to Nanoproducts", Degussa ScienceNewsletter No. 8, 2004, pp. 12-16.

Coating Generation: Vaporization of Particles in Plasma Spraying and Splat Formation M. Vardelle, A. Vardelle, K-I li, P. Fauchais, Universite de Limoges, 123 Avenue A. Thomas 87000, Limoges, F., Pure & Chem, vol. 68, No. 5, pp. 1093-1099, 1996.

H. Konrad et al., "Nanostructured Cu-Bi Alloys Prepared by Co-Evaporation in a Continuous Gas Flow," NanoStructured Materials, vol. 7, No. 6, Apr. 1996, pp. 605-610.

M.Vardelle et al., "Experimental Investigation of Powder Vaporization in Thermal Plasma Jets," Plasma Chemistry and Plasma Processing, vol. 11, No. 2, Jun. 1991, pp. 185-201.

P. Fauchais et al., "Plasma Spray: Study of the Coating Generation," Ceramics International, Elsevier, Amsterdam, NL, vol. 22, No. 4, Jan. 1996, pp. 295-303.

P. Fauchais et al., "Les Dépôts Par Plasma Thermique," Revue Generale De L'Electricitie, RGE. Paris, FR, No. 2, Jan. 1993, pp. 7-12.

P. Fauchais et al, "La Projection Par Plasma: Une Revue," Annales De Physique, vol. 14, No. 3, Jun. 1989, pp. 261-310.

* cited by examiner

MICROWAVE PURIFICATION PROCESS

CROSS-REFERENCE TO RELATED APPLICATIONS

The present application claims priority to U.S. Provisional Application Ser. No. 60/928,946, filed May 11, 2007, entitled "MATERIAL PRODUCTION SYSTEM AND METHOD," which is hereby incorporated by reference as if set forth herein.

FIELD OF THE INVENTION

The present invention relates to the field of materials purification. More specifically, the present invention relates to a microwave-based purification process and system.

BACKGROUND OF THE INVENTION

In the powdered materials industry, there has become an increased interest in purer and purer powders. There are a variety of reasons for this interest. In the semiconductor industry, and more specifically the hard disk industry, there is a need for purer and purer metals. Components such as ¾" inch hard drives in cell phones and MP3 players can have up to six layers of metal on the mini-hard drives in order to achieve the storage capacity needed for video and other data. One of the metals that is used for coating is ruthenium. Here, the oxygen content is critical. If the oxygen content is too high, it can result in the formation of ruthenium-oxides, which are non-conductive. Non-conductivity poses problems when trying to store data.

Figure 1:
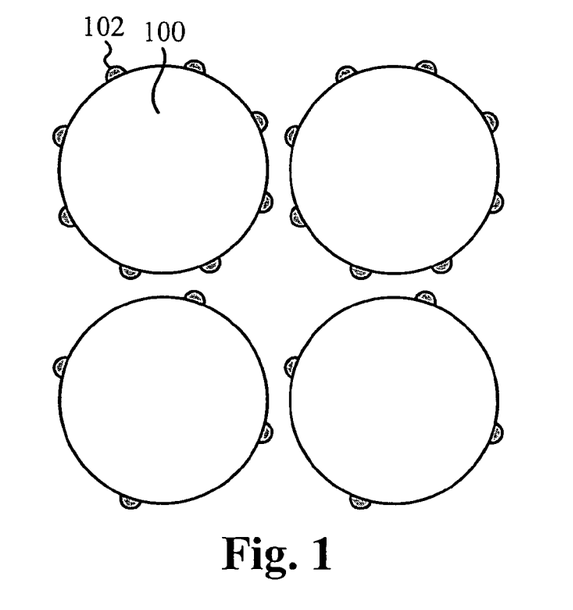
FIG. 1 illustrates a target powder having an oxygen content.

FIG. 1 illustrates one example of powder particles 100 that are typically used in the materials industry. These powder particles 100 typically contain impurities, such as oxygen content 102 disposed around their core. The industry is looking for purification levels equal to or less than 200 ppm of oxygen in the starting powders. Currently, one attempted solution is to place the powder in a vacuum furnace or in a hydrogen-fired vacuum furnace on a tray. The furnace is brought up to relatively high temperatures. The oxygen content (and moisture) is desorbed from the powder. Hydrogen can flow over the powder to grab and remove the oxygen and moisture content, which is pumped out, leaving a purer powder.

The downside of these furnace technologies is that they require the use of high temperatures for a long period of time. One problem with this requirement is that it places a limitation on the minimum size of grain that can be purified. The smaller the grain size, the lower the sintering temperature is for the powder, thus making small grain powders difficult to purify using these technologies. What is needed is a more cost effective technology that allows relatively small grains to be purified without sintering.

These issues are important to the powder industry in general. Cutting tools can be formed from powders, such as tungsten-carbide, tungsten-nitride and the like. However, the powders often contain oxygen, sometimes in the form of thin oxygen layers formed around each particle. In sintering the powders together to form the cutting tools, it is desirable to maintain the powder-like nature. However, it is important to minimize the void between the particles. If the void is too big, the structural integrity of the end product suffers. If there is too much oxygen, the particles will not sufficiently sinter together. When using a cutting tool made from powders having these deficiencies, the lack of structural integrity can cause the tool to fracture. What is needed is a better way to take oxygen out of powders, reduce the voids, and prepare the powders for sintering.

Figure 2:
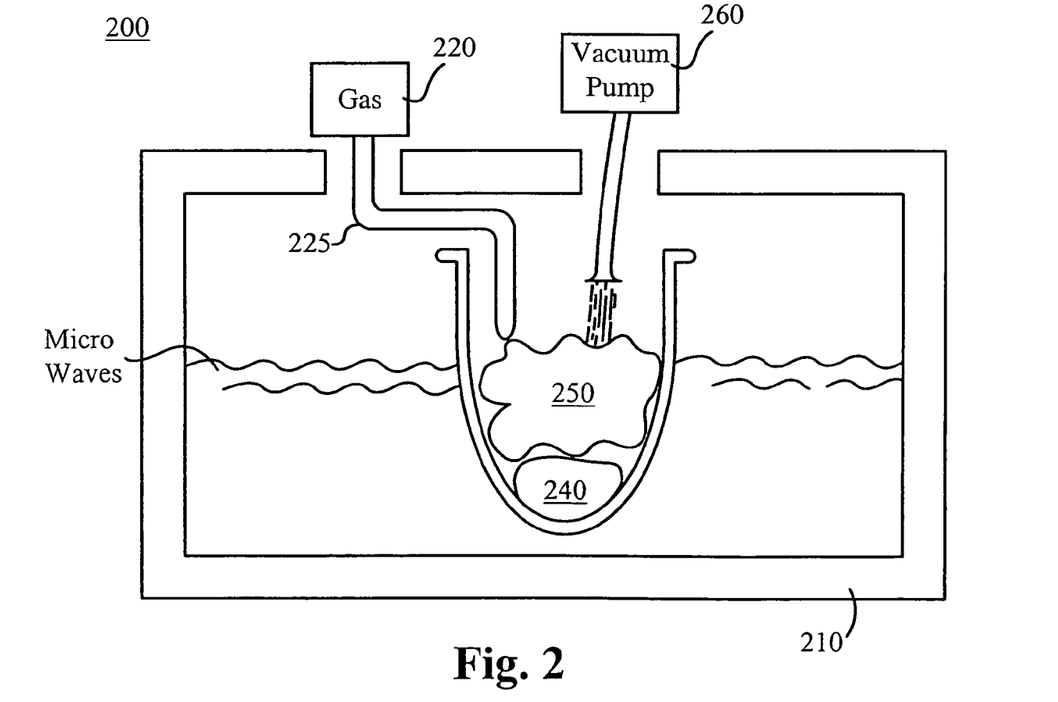
FIG. 2 illustrates a prior art powder purification system.

FIG. 2 illustrates one system 200 that has be used to try and purify powders. Here, the target powder 240 (for example, boron) is disposed in a crucible 230 that is housed within a microwave production chamber 210, such as a microwave oven. Hydrogen gas flows from a gas supply system 220 into the microwave production chamber 210 via a conduit or tube 225. As the hydrogen gas flows into the microwave production chamber 210 and the crucible 230, the microwave production chamber 210 generates and applies microwaves to the hydrogen gas, thereby forming a plasma 250 and creating hydrogen radicals, which flow over the target powder 240 and are drawn out of the chamber 210 along with oxygen content from the target powder. This drawing force is supplied by a vacuum pump 260. Although this system removes a portion of the oxygen content, there is a problem with having the target powder being exposed to the energy of the microwaves. In this configuration, the target powder can loosely couple to the microwave and heat up. This parasitic heating can result in the powder being crystallized. In circumstances where amorphous powders are preferred, this crystallization is highly undesirable.

Therefore, what is needed in the art is an efficient and cost effective system and method of removing oxygen content from a target powder, while avoiding or minimizing any parasitic heating.

SUMMARY OF THE INVENTION

In one aspect of the present invention, a method of purifying a target powder having an oxygen content is provided. The method comprises flowing hydrogen gas through a microwave production chamber and applying microwaves to the hydrogen gas as the hydrogen gas flows through the microwave production chamber, thereby forming hydrogen radicals from the hydrogen gas. The hydrogen radicals flow out of the microwave production chamber to a target powder disposed outside of the microwave production chamber, where they are applied to the target powder, thereby removing a portion of the oxygen content from the target powder.

In another aspect of the present invention, a microwave purification system is provided. The system comprises a gas supply system configured to provide hydrogen gas and a microwave production chamber fluidly coupled to the gas supply system. The microwave production chamber is configured to receive hydrogen gas from the gas supply system and apply microwaves to the hydrogen gas, thereby forming hydrogen radicals. A target chamber is disposed outside of and fluidly coupled to the microwave production chamber. The target chamber is configured to receive the hydrogen radicals from the microwave production chamber and apply the hydrogen radicals to a target powder disposed within the target chamber, thereby removing a portion of oxygen content from the target powder.

In preferred embodiments, the target powder is housed within a target chamber. The hydrogen radicals flow into the target chamber and remove oxygen content from the target powder. The removed oxygen content then flows out of the target chamber.

In preferred embodiments, applying the hydrogen radicals to the target powder comprises the steps of agitating the target powder within the target chamber and flowing the hydrogen radicals through the target chamber as the target powder is being agitated.

Preferably, the target chamber houses a rotatable paddle wheel having an interior circumference and a plurality of paddles disposed in an annular configuration along the interior circumference. The target powder is disposed in the paddle wheel and the wheel is rotated as the hydrogen radical flow through the target chamber. In a preferred embodiment, the rotatable paddle wheel comprises a first end through which the hydrogen radicals enter and a second end through which the removed oxygen content exits. The rotatable paddle wheel extends from the first end to an expanding frusto-conical surface to a substantially cylindrical surface to a narrowing frusto-conical surface to the second end. The plurality of paddles are disposed on the substantially cylindrical surface.

In certain embodiments, the target chamber is heated prior to or during the step of applying the hydrogen radicals to the target powder. Preferably, the target chamber is heated to a temperature equal to or less than 1200 degrees Fahrenheit. Furthermore, the target powder can be heated prior to the step of applying the hydrogen radicals to the target powder.

In preferred embodiments, the step of flowing the hydrogen gas comprises applying a vacuum force to the hydrogen gas and the step of flowing the hydrogen radicals comprises applying a vacuum force to the hydrogen radicals.

Additionally, the step of applying microwaves to the hydrogen gas can result in the formation of hydrogen ions within the microwave production chamber. In certain embodiments, the method further comprises the steps of flowing the hydrogen ions out of the microwave production chamber to the target powder disposed outside of the microwave production chamber and applying the hydrogen ions to the target powder.

It is contemplated that a wide variety of target powder can be used in the present invention. Such target powders include, but are not limited to, boron and ruthenium.

DETAILED DESCRIPTION OF THE INVENTION

The description below concerns several embodiments of the invention. The discussion references the illustrated preferred embodiment. However, various modifications to the described embodiments will be readily apparent to those skilled in the art and the generic principles herein may be applied to other embodiments. Therefore, the scope of the present invention is not limited to either the illustrated embodiment, nor is it limited to those discussed. To the contrary, the scope should be interpreted as broadly as possible based on the language of the Claims section of this document.

In the following description, numerous details and alternatives are set forth for purpose of explanation. However, one of ordinary skill in the art will realize that the invention can be practiced without the use of these specific details. In other instances, well-known structures and devices are shown in block diagram form in order not to obscure the description of the invention with unnecessary detail.

This disclosure refers to both particles and powders. These two terms are equivalent, except for the caveat that a singular "powder" refers to a collection of particles. The present invention may apply to a wide variety of powders and particles. Powders that fall within the scope of the present invention may include, but are not limited to, any of the following: (a) nano-structured powders (nano-powders), having an average grain size less than 250 nanometers and an aspect ratio between one and one million; (b) submicron powders, having an average grain size less than 1 micron and an aspect ratio between one and one million; (c) ultra-fine powders, having an average grain size less than 100 microns and an aspect ratio between one and one million; and (d) fine powders, having an average grain size less than 500 microns and an aspect ratio between one and one million.

The present invention will be readily understood by the following detailed description in conjunction with the accompanying drawings. To facilitate this description, like reference numerals designate like elements.

Figure 3:
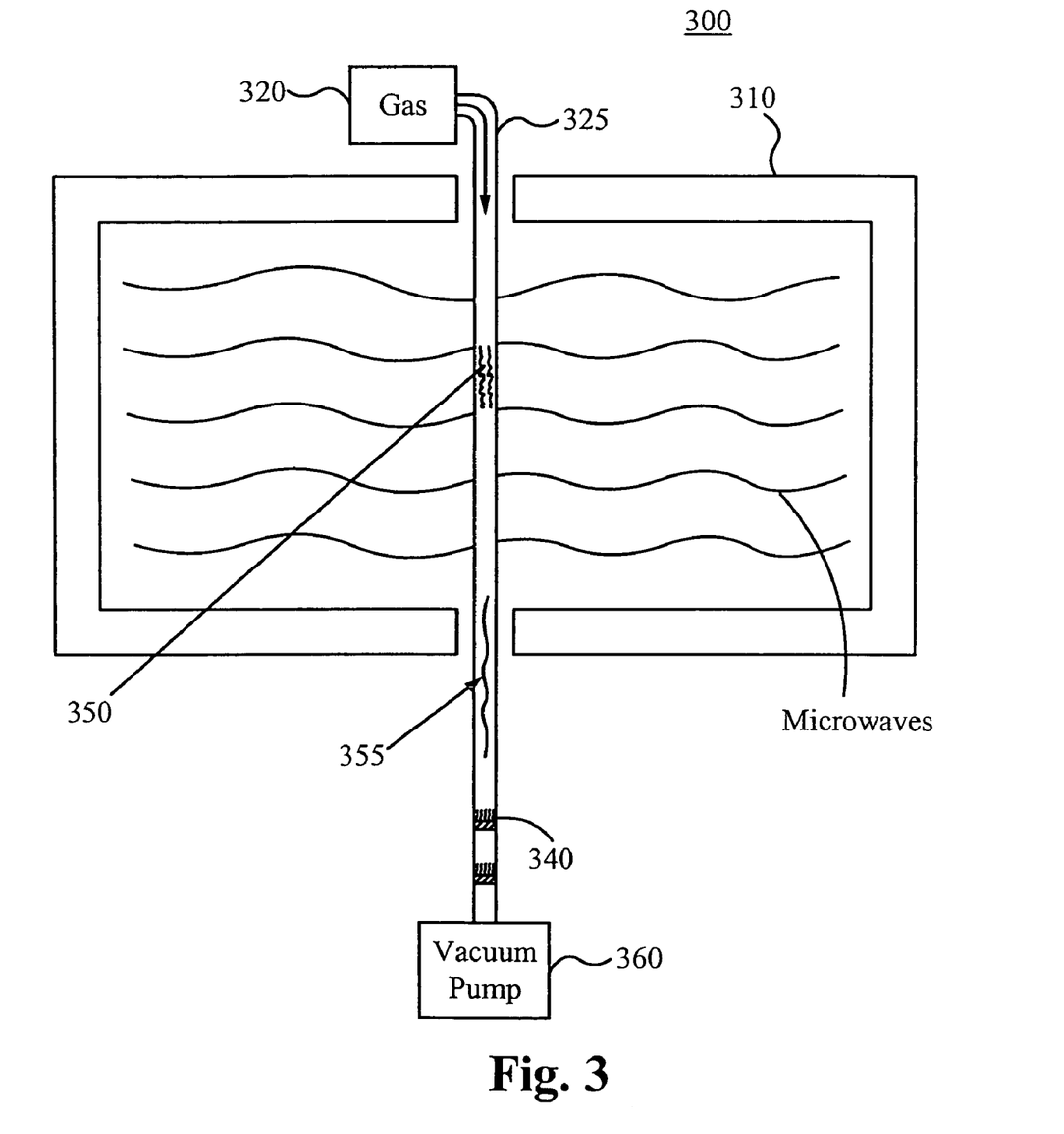
FIG. 3 illustrates one embodiment of a microwave purification system in accordance with the principles of the present invention.

FIG. 3 illustrates one embodiment of a microwave purification system 300 in accordance with the principles of the present invention. The system 300 comprises a microwave production chamber 310 configured to generate microwaves, a gas supply system 320 configured to provide a gas (preferably hydrogen), and a vacuum pump 360 fluidly coupled to the gas supply system 320 via a conduit or tube 325 that runs into and out of the microwave production chamber 310.

In operation, the vacuum pump 360 draws the hydrogen gas from the gas supply system 320 through the conduit 325 and into the microwave production chamber 310. Here, the microwave production chamber 310 produces microwaves, which are applied to the hydrogen gas to strike a plasma 350. As a result, hydrogen radicals 355 are formed. The hydrogen radicals 355 are then drawn out of the microwave production chamber 310 by the vacuum pump 360 and are applied to the target powder 340, which is disposed out of the microwave production chamber 310. The target powder 340 can be contained within a crucible in fluid communication with the conduit 325. The hydrogen radicals 355 react with the oxygen content of the powder 340, thereby disassociating the oxygen content from the powder. The removed oxygen content can then be drawn further away from the powder by the vacuum pump.

In addition to the hydrogen radicals 355, it is contemplated that hydrogen ions (i.e., hydrogen plasma) can also be formed in the microwave production chamber 310. At a low enough pressure, the glow discharge of the hydrogen plasma 355 can be drawn out to the target powder 340 by the vacuum pump 360. The hydrogen plasma can be applied to the target powder 340 to aid in the removal of the oxygen content.

By disposing the target powder 340 outside of the microwave production chamber 310 (i.e., out of the pathway of the microwaves), the system 300 can subject the target powder 340 to hydrogen radicals and ions, while avoiding the microwave energy and the parasitic heating associated with it.

Additionally, it is contemplated that the target powder 340 can be heating at a controlled rate prior to or during its exposure to the hydrogen radicals. This heating can aid in the chemical reactivity of the hydrogen and ablate or drive off moisture on the target powder 340.

Figure 4:
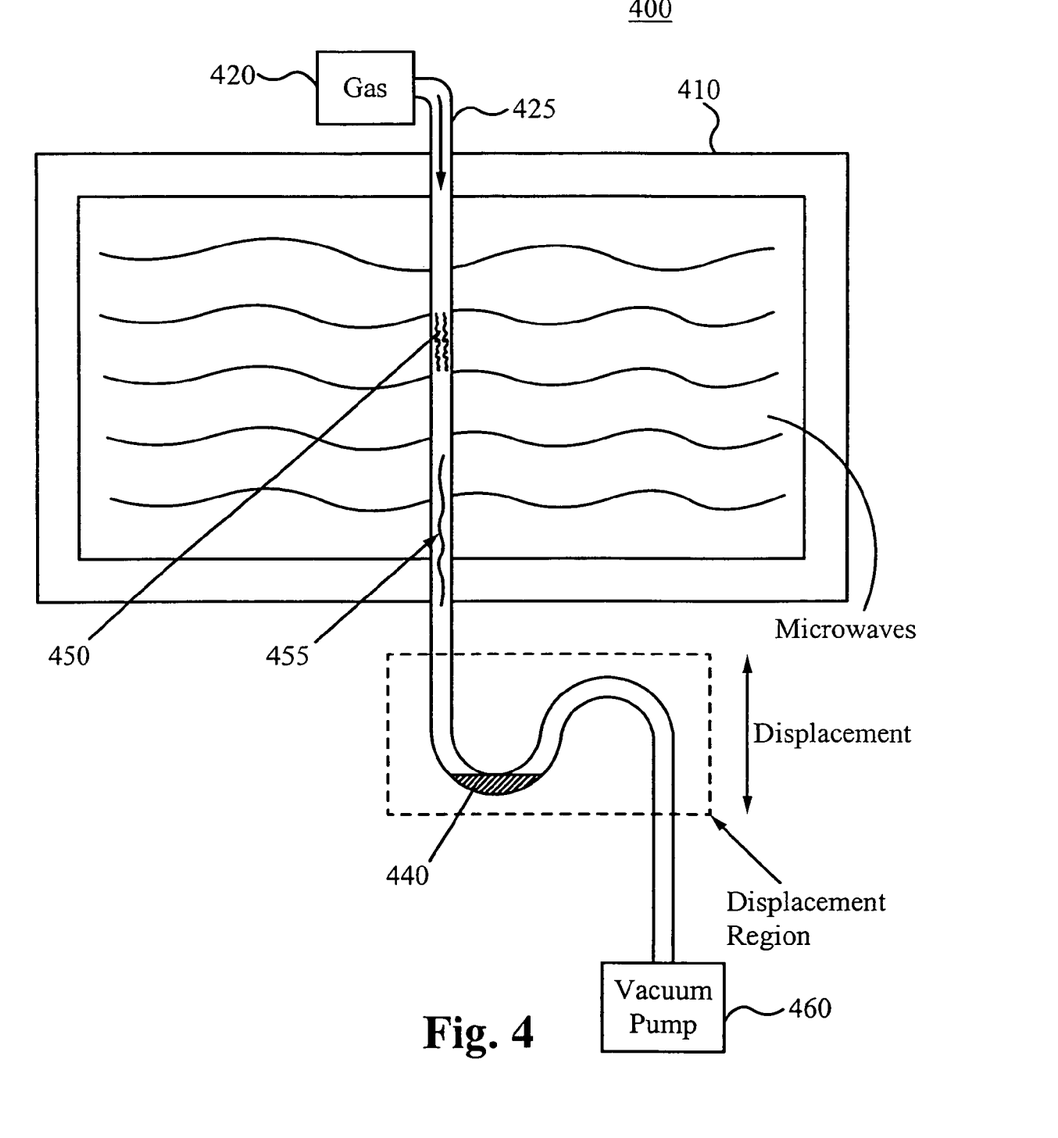
FIG. 4 illustrates another embodiment of a microwave purification system in accordance with the principles of the present invention.

FIG. 4 illustrates another embodiment of a microwave purification system 400 in accordance with the principles of the present invention. The system 400 comprises a microwave production chamber 410 configured to generate microwaves, a gas supply system 420 configured to provide a gas (preferably hydrogen), and a vacuum pump 460 fluidly coupled to the gas supply system 420 via a conduit or tube 425 that runs into and out of the microwave production chamber 410. Upon exiting the microwave production chamber 410, the conduit 425 can gooseneck or bend within a displacement region. In a preferred embodiment, the conduit 425 is configured to be agitated in the direction of the displacement arrows in order to shake up the target powder 440.

In operation, the vacuum pump 460 draws the hydrogen gas from the gas supply system 420 through the conduit 425 and into the microwave production chamber 410. Here, the microwave production chamber 410 produces microwaves, which are applied to the hydrogen gas to strike a plasma 450. As a result, hydrogen radicals 455 are formed. The hydrogen radicals 455 are then drawn out of the microwave production chamber 410 by the vacuum pump 460 and are applied to the target powder 440, which is disposed out of the microwave production chamber 410. The target powder 440 can be contained within a crucible in fluid communication with the conduit 425. The hydrogen radicals react with the oxygen content of the powder 440, thereby disassociating the oxygen content from the powder. The removed oxygen content can then be drawn further away from the powder by the vacuum pump.

In addition to the hydrogen radicals, it is contemplated that hydrogen ions (i.e., hydrogen plasma) can also be formed in the microwave production chamber 410. At a low enough pressure, the glow discharge of the hydrogen plasma 450 can be drawn out to the target powder 440 by the vacuum pump 460. The hydrogen plasma can be applied to the target powder 440 to aid in the removal of the oxygen content.

By disposing the target powder 440 outside of the microwave production chamber 410 (i.e., out of the pathway of the microwaves), the system 400 can subject the target powder 440 to hydrogen radicals and ions, while avoiding the microwave energy and the parasitic heating associated with it.

Additionally, it is contemplated that the target powder 440 can be heating at a controlled rate prior to or during its exposure to the hydrogen radicals. This heating can aid in the chemical reactivity of the hydrogen and ablate or drive off moisture on the target powder 440.

Although not shown in FIGS. 3 and 4, it is contemplated that the conduits can run through the microwave production chambers through airtight seals.

Figure 5:
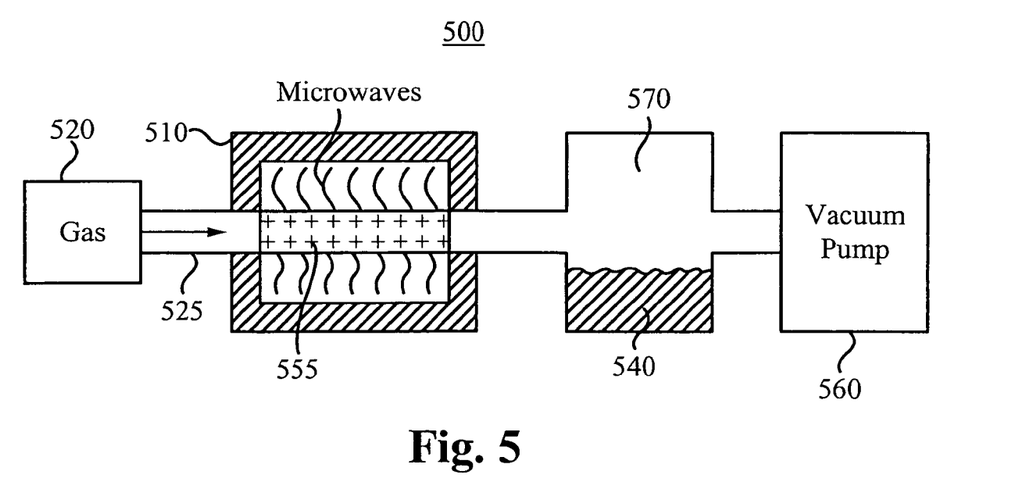
FIG. 5 illustrates yet another embodiment of a microwave purification system in accordance with the principles of the present invention.

FIG. 5 illustrates yet another embodiment of a microwave purification system 500 in accordance with the principles of the present invention. The system 500 comprises a microwave production chamber 510 configured to generate microwaves, a gas supply system 520 configured to provide a gas (preferably hydrogen), a target chamber 570 fluidly coupled to the microwave production chamber 510, preferably via a conduit or tube 525 that runs into and out of the microwave production chamber 510. A vacuum pump 560 is fluidly coupled to the target chamber 570, the microwave production chamber 510, and the gas supply system 520.

The target powder 540 is housed within the target chamber 570. In a preferred embodiment, the target chamber 570 is configured to agitate the target powder 540. Such agitation can be achieved in a variety of ways.

In operation, the vacuum pump 560 draws the hydrogen gas from the gas supply system 520 through the conduit 525 and into the microwave production chamber 510. Here, the microwave production chamber 510 produces microwaves, which are applied to the hydrogen gas to strike a plasma. As a result, hydrogen radicals 555 are formed. The hydrogen radicals 555 are then drawn out of the microwave production chamber 510 by the vacuum pump 560 and into the target chamber 570, where they are applied to the target powder 540 disposed therein. Some of the hydrogen radicals 555 flow straight through the target chamber 570 without reacting with the oxygen content of the target powder 540. However, some of the hydrogen radicals 555 do react with the oxygen content of the target powder 540, thereby disassociating the oxygen content from the powder. The removed oxygen content can then be drawn out of the target chamber 570 by the vacuum pump.

In order to maximize exposure of the target powder 540 to the hydrogen radicals 555, the target chamber preferably agitates the target powder 540 as the hydrogen radicals 555 flow through the target chamber 570. In a preferred embodiment, the target chamber 570 agitates the target powder 540 in such a way as to cause the powder to pass through the flow path of the hydrogen radicals.

In addition to the hydrogen radicals, it is contemplated that hydrogen ions (i.e., hydrogen plasma) can also be formed in the microwave production chamber 510. At a low enough pressure, the glow discharge of the hydrogen plasma can be drawn out to the target powder 540 by the vacuum pump 460. In a preferred embodiment, the hydrogen plasma discussed in FIGS. 3-5 is drawn out at a pressure equal to or less than approximately $1/350$ of an atmosphere. The hydrogen plasma can be applied to the target powder 540 to aid in the removal of the oxygen content.

By disposing the target powder 540 outside of the microwave production chamber 510 (i.e., out of the pathway of the microwaves), the system 500 can subject the target powder 540 to hydrogen radicals and ions, while avoiding the microwave energy and the parasitic heating associated with it.

Additionally, it is contemplated that the target powder 540 can be heating at a controlled rate prior to or during its exposure to the hydrogen radicals. This heating can aid in the chemical reactivity of the hydrogen and ablate or drive off moisture on the target powder 540.

Figure 6:
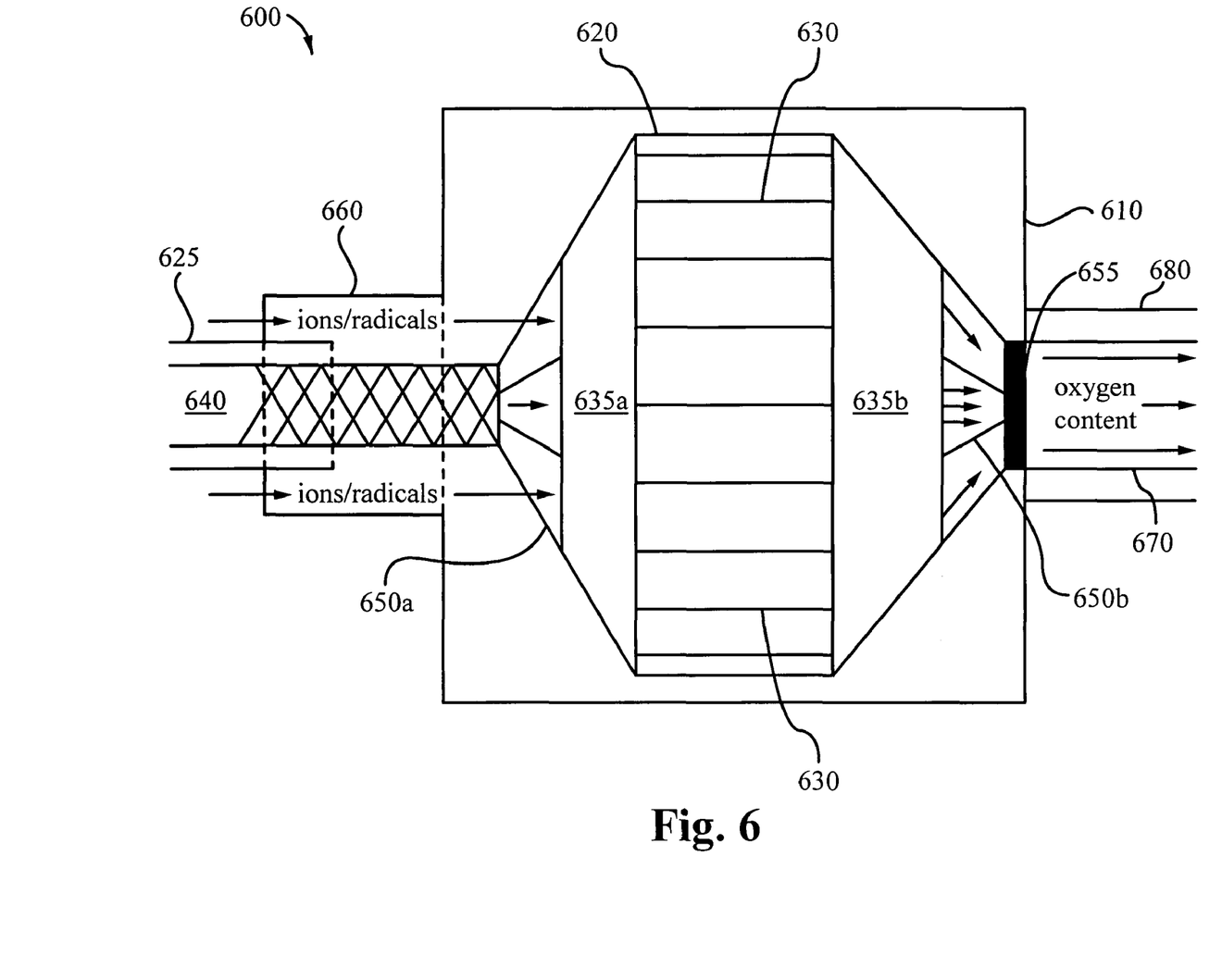
FIG. 6 illustrates one embodiment of a target chamber in accordance with the principles of the present invention.

FIG. 6 illustrates one embodiment of a target chamber 600 in accordance with the principles of the present invention. In a preferred embodiment, the target chamber comprises a casing 610, preferably formed of metal so that it can be heated at a controlled rate as discussed above. The target chamber 600 is configured to agitate the target powder as the hydrogen radicals/ions flow through it via a gas supply conduit 660 fluidly coupled to the interior of the casing 610. Preferably, the gas supply conduit 660 is fluidly coupled to one of the microwave production chambers in FIGS. 3-5.

Within the casing 610 is housed a paddle wheel 620 configured to be rotated about a central axis. It is contemplated that the paddle wheel 620 can be rotated in a variety of ways, whether they be manual or automated. In a preferred embodiment, paddle wheel 620 is rotated by a shaft 640 to which it is coupled. Preferably, the interior of the casing 610 can be sealed off from any exterior contamination. The shaft 640 can be disposed within a rotary seal 625 that is connected to the gas supply conduit 660, thereby allowing the shaft 640 to rotate, while still preventing any contamination of the target powder within the casing 610 from external impurities.

In a preferred embodiment, the paddle wheel 620 comprises a first end through which the hydrogen radicals enter and a second end through which the removed oxygen content exits. The paddle wheel 620 preferably extends from the first end to an expanding frusto-conical surface 635a, to a substantially cylindrical surface, to a narrowing frusto-conical surface 635b, and finally to the second end. The frusto-conical surfaces aid in preventing the target powder from being drawn out of the paddle wheel 620 and the casing 610.

Figure 7:
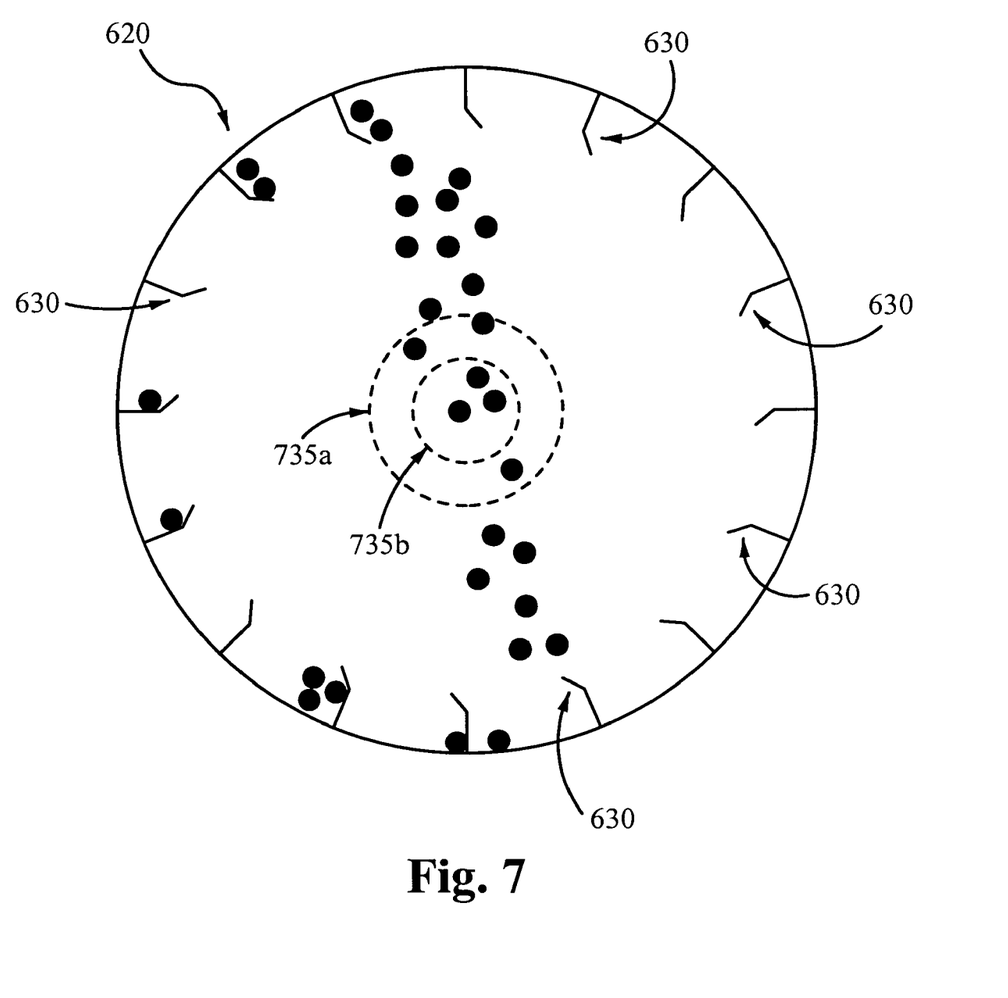
FIG. 7 illustrates one embodiment of a rotatable paddle wheel in accordance with the principles of the present invention.

The paddle wheel 620 has an interior circumference and a plurality of paddles 630 disposed in an annular configuration along the interior circumference. The paddles 630 can be uniformly-spaced or irregularly-spaced apart. During operation, the target powder is disposed in the paddle wheel 620. As the paddle wheel 620 rotates about its central axis, the paddles 630 lift a portion of the target powder up, then drop the target powder down through a location proximate the central axis in line with the flow if the radicals/ions, thereby maximizing the target powder's exposure to the radicals/ions. In a preferred embodiment, the plurality of paddles are disposed on the substantially cylindrical surface. As seen in FIG. 7, which is a view of the paddle wheel 620 from the perspective of looking through the gas supply conduit 660 in the direction of the radical/ion flow, the paddles 630 can be slightly angled or have a minor hook in order to aid in the lifting of the target powder.

Shaft 640 can be coupled to the first end of the paddle wheel 620 using spokes 650a. The second end of the paddle wheel 620 can be rotatably coupled to an oxygen content outlet 670 using spokes 650b and a rotary seal 655. An additional conduit 680 can be coupled to the casing 610 so as to cover oxygen content outlet 670. Oxygen content conduit 670 preferably extends into the casing 610 and is configured to receive the oxygen content flowing out of the paddle wheel 620 and the casing 610.

Referring back to FIG. 7, dotted line 735a represents the opening at the narrowest end of frusto-conical surface 635a (from FIG. 6) and dotted line 735b represents the opening at the narrowest end of frusto-conical surface 635b (from FIG. 6). In a preferred embodiment, the opening 735b is smaller in diameter than the opening 735a, as it can be helpful to minimize the exit opening 735b in order to prevent target powder from being drawn out of the paddle wheel and the casing. However, it is contemplated that a variety of size configurations can be employed.

Figure 8:
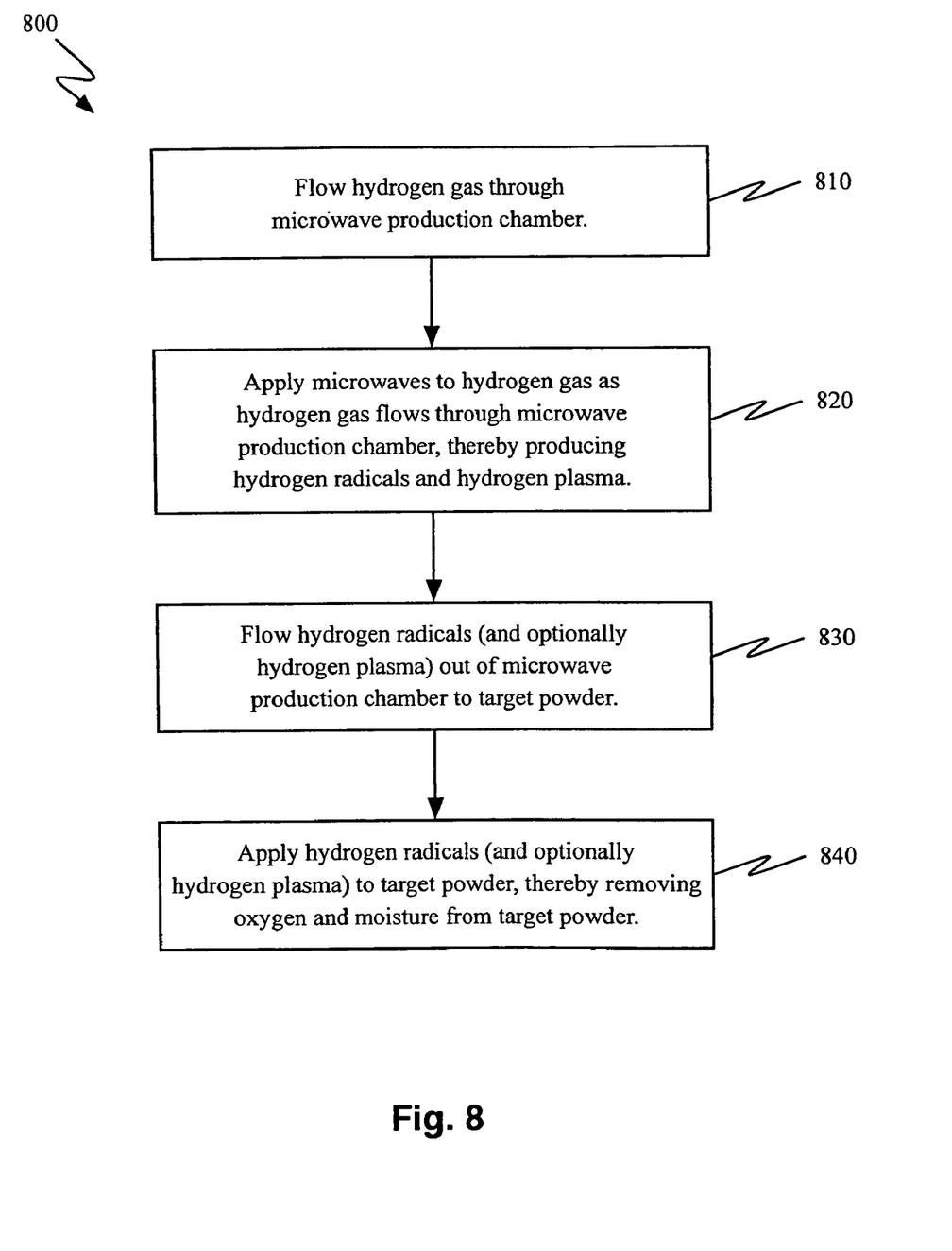
FIG. 8 is a flowchart illustrating one embodiment of a method of purifying powder in accordance with the principles of the present invention.

FIG. 8 is a flowchart illustrating one embodiment of a method 800 of purifying powder in accordance with the principles of the present invention. As would be appreciated by those of ordinary skill in the art, the protocols, processes, and procedures described herein may be repeated continuously or as often as necessary to satisfy the needs described herein. Additionally, although the steps of method 800 are shown in a specific order, certain steps may occur simultaneously or in a different order than is illustrated. Accordingly, the method steps of the present invention should not be limited to any particular order unless either explicitly or implicitly stated.

At step 810, hydrogen gas flows through a microwave production chamber. In a preferred embodiment, the hydrogen gas is supplied by a gas supply system and is drawn out by a vacuum pump through a conduit.

At step 820, the microwave production chamber generates and applies microwaves to the hydrogen gas as the hydrogen gas flows through the microwave production chamber, thereby forming hydrogen radicals from the hydrogen gas. Hydrogen ions/plasma can be formed as well.

At step 830, the hydrogen radicals, and possibly the hydrogen ions/plasma flow out of the microwave production chamber to a target powder disposed outside of the microwave production chamber. In a preferred embodiment, the target powder is housed within a target chamber, preferably configured to agitate the target powder as discussed above.

At step 840, the hydrogen radicals, and possibly the hydrogen ions/plasma, are applied to the target powder. The hydrogen ions react with oxygen content of the target powder, thereby removing a portion of the oxygen content from the target powder. This removed oxygen content can then be drawn away from the target powder, preferably out of the target chamber.

The present invention has been described in terms of specific embodiments incorporating details to facilitate the understanding of the principles of construction and operation of the invention. As such, references herein to specific embodiments and details thereof are not intended to limit the scope of the claims appended hereto. It will be apparent to those skilled in the art that modifications can be made to the embodiments chosen for illustration without departing from the spirit and scope of the invention.

What is claimed is:

1. A method of purifying a target powder having an oxygen content, the method comprising:
   flowing hydrogen gas through a microwave production chamber;
   applying microwaves to the hydrogen gas as the hydrogen gas flows through the microwave production chamber, thereby forming hydrogen radicals from the hydrogen gas;
   flowing the hydrogen radicals out of the microwave production chamber to a target powder disposed outside of the microwave production chamber; and
   applying the hydrogen radicals to the target powder, thereby removing a portion of the oxygen content from the target powder.

2. The method of claim 1, wherein the target powder is housed within a target chamber and the step of applying the hydrogen radicals to the target powder further comprises the steps of:
   flowing the hydrogen radicals into the target chamber; and
   flowing the removed oxygen content out of the target chamber.

3. The method of claim 2, wherein the step of applying the hydrogen radicals to the target powder further comprises the steps of:
   agitating the target powder within the target chamber; and
   flowing the hydrogen radicals through the target chamber as the target powder is being agitated.

4. The method of claim 3, wherein the target chamber houses a rotatable paddle wheel having an interior circumference and a plurality of paddles disposed in an annular configuration along the interior circumference, the target powder disposed in the paddle wheel, the step of agitating the target powder comprising the step of rotating the paddle wheel.

5. The method of claim 4, wherein the rotatable paddle wheel comprises a first end through which the hydrogen radicals enter and a second end through which the removed oxygen content exits, the rotatable paddle wheel extending from the first end to an expanding frusto-conical surface to a substantially cylindrical surface to a narrowing frusto-conical surface to the second end, the plurality of paddles being disposed on the substantially cylindrical surface.

6. The method of claim 4, further comprising the step of heating the target chamber prior to the step of applying the hydrogen radicals to the target powder, wherein the target chamber is heated to a temperature equal to or less than 1200 degrees Fahrenheit.

7. The method of claim 1, further comprising the step of heating the target powder prior to the step of applying the hydrogen radicals to the target powder.

8. The method of claim 1, wherein the step of flowing the hydrogen gas comprises applying a vacuum force to the hydrogen gas and the step of flowing the hydrogen radicals comprises applying a vacuum force to the hydrogen radicals.

9. The method of claim 1, the step of applying microwaves to the hydrogen gas results in the formation of hydrogen ions within the microwave production chamber, and the method further comprises the steps of:

flowing the hydrogen ions out of the microwave production chamber to the target powder disposed outside of the microwave production chamber; and applying the hydrogen ions to the target powder.

10. The method of claim 1, wherein the target powder is boron.

11. The method of claim 1, wherein the target powder is ruthenium.

* * * * *